United States Patent [19]

Wheeler

[11] Patent Number: 4,532,918
[45] Date of Patent: Aug. 6, 1985

[54] ENDOSCOPE SIGNAL LEVEL CONTROL
[75] Inventor: Robert C. Wheeler, Skaneateles, N.Y.
[73] Assignee: Welch Allyn Inc., Skaneateles Falls, N.Y.
[21] Appl. No.: 540,138
[22] Filed: Oct. 7, 1983
[51] Int. Cl.³ .............................................. A61B 1/04
[52] U.S. Cl. ........................................ 128/6; 358/98; 358/168
[58] Field of Search ............... 128/6, 7, 8, 9; 358/98, 358/39, 41, 42, 161, 163, 164, 168, 169, 170, 174, 176, 179

[56] References Cited
U.S. PATENT DOCUMENTS

| Re. 31,289 | 6/1983 | Moore et al. ............................ 128/6 |
| Re. 31,290 | 6/1983 | Moore et al. ............................ 128/6 |
| 3,009,989 | 11/1961 | Ahrons et al. .................. 358/168 X |
| 3,879,637 | 4/1975 | Woodworth .................... 358/170 X |
| 3,970,777 | 7/1976 | Bradford et al. ................ 358/170 X |
| 4,074,306 | 2/1978 | Kakinuma et al. ................. 128/6 X |
| 4,423,436 | 12/1983 | Kimura .................................. 358/98 |
| 4,475,539 | 10/1984 | Konomura ............................... 128/6 |

Primary Examiner—William H. Grieb
Attorney, Agent, or Firm—Bruns and Wall

[57] ABSTRACT

Apparatus for controlling the video signal level of a color endoscope to prevent the picture from blooming as the viewing head of the instrument is moved toward and away from a confined target. Circuit means are provided for automatically controlling both the amplified gain of the signal and the intensity of the illumination used to light the target during a series of color imaging sequences so that the color balance of the system is not disturbed.

7 Claims, 2 Drawing Figures

4,532,918

ENDOSCOPE SIGNAL LEVEL CONTROL

BACKGROUND OF THE INVENTION

This invention relates to a video-equipped endoscope that utilizes sequential color imagery to produce a full-color video picture of a remote target and, in particular, to an automatic signal level control for use in a video-equipped endoscope.

With the development of charged couple devices (CCD), it is now possible to equip the insertion tube head of an endoscope with an extremely small video camera that enables the head to be positioned within relatively confined regions that have heretofore been inaccessible to this type of viewing equipment. The video camera generally contains a single black and white CCD image sensor that integrates the light imaged onto its surface while recording a given picture of the target. In order to produce a full-color video picture of the target, the target is illuminated sequentially with light of primary colors to produce color separated images. Typically the primary colors of red, green and blue are used in the video system. The color separated images, after being recorded by the image sensor, are clocked out in the form of video signals to a downstream processor that places the color information in a format which is compatible with most video systems.

In U.S. Pat. No. 4,074,306 to Kakinuma et al, there is disclosed a video-equipped endoscope system employing a solid state image sensor. Color separation is created by means of a filter wheel that is adapted to rotate red, green and blue filters through the beam of a single arc lamp used to illuminate the target. The recorded images are processed in sequence and laid down one over the other upon a Braun tube. Beyond the disadvantages relating to sequentially laying down color-separated images upon a Braun tube, the Kakinuma et al system makes no provision for proportionally balancing the color separated images. Consequently, when the images are brought together to form a video picture, the picture may not faithfully reflect the original colors found in the target region. The Kakinuma et al endoscope, therefore, has little use as a medical diagnostic instrument.

In a co-pending U.S. application Ser. No. 487,070 filed in the name of Sarofeen et al, there is disclosed a color-balancing system for use in a video-equipped endoscope system utilizing a filter wheel to create color-separated images. In this particular system, an arc lamp is employed to illuminate the target region. The amount of charge placed upon the discharge capacitor of the lamp is closely controlled in order to limit the amount of illumination received by the target during each color-imaging sequence. The amount of illumination utilized during each color-imaging sequence is manually preset to attain a proper balance between the colors used to create the video picture. Once preset, the system will automatically maintain the three-color illumination levels constant until such time as the levels are readjusted.

The viewing head of the video endoscope, particularly when used in a medical application, is required to operate within a very confined region containing little, if any, ambient light. The light used to illuminate the target is generally brought into the target region from a remote source via fiber bundles. However, as the head is moved towards or away from the target, the amount of reflected light recorded by the CCD image sensor changes dramatically. Although an automatic gain control can be included in the video system, this in itself may not be sufficient to prevent the picture from blooming when the CCD image sensor reaches a full well condition. As will be explained in greater detail below, the present invention is designed to act in conjunction with an automatic gain control circuit to reduce the output of the illumination lamp without disturbing the proportional color balance of the color separated images.

SUMMARY OF THE INVENTION

It is an object of the present invention to improve a video endoscope for providing full-color video pictures of a remote target.

A further object of the present invention is to provide an automatic light control for a video endoscope.

Another object of the present invention is to automatically control the target illumination intensity of a color video endoscope without disturbing the color balance of the color-separated images.

Yet another object of the present invention is to allow the video camera of a color video endoscope to be positioned close to the target without the danger of the video picture blooming.

A still further object of the present invention is to prevent a solid state image sensor located in the viewing head of a video endoscope from reaching a full well condition.

These and other objects of the present invention are attained by means of a video endoscope capable of providing a full-color video picture of a remote target using a single illumination lamp that is arranged to act in association with a solid state CCD image sensor for recording color target information. A color wheel is used to bring red, green and blue filters sequentially to the illumination beam of the lamp during each video field in order to create three color-separated images of the target. The intensity of the lamp output during each color imaging sequence is manually adjusted so that the color-separated images are proportionally balanced to provide an accurate picture of the original target information. Both the gain of the video amplifier section and the intensity of the illumination lamp are controlled automatically in response to changes in the video signal levels in order to achieve high quality images while simultaneously operating the image sensor within an optimum range that is well above background noise but below the saturation level of the image sensor.

BRIEF DESCRIPTION OF THE DRAWINGS

For a better understanding of these and other objects of the present invention, reference is had to the following detailed description thereof which is to be read in conjunction with the accompanying drawings, wherein:

FIG. 1 consists of Figs. 1a and 1b which are orientated as shown and which together illustrate circuitry embodying the teachings of the present invention suitable for use in a video-equipped endoscope;

DESCRIPTION OF THE INVENTION

Figure 1A:
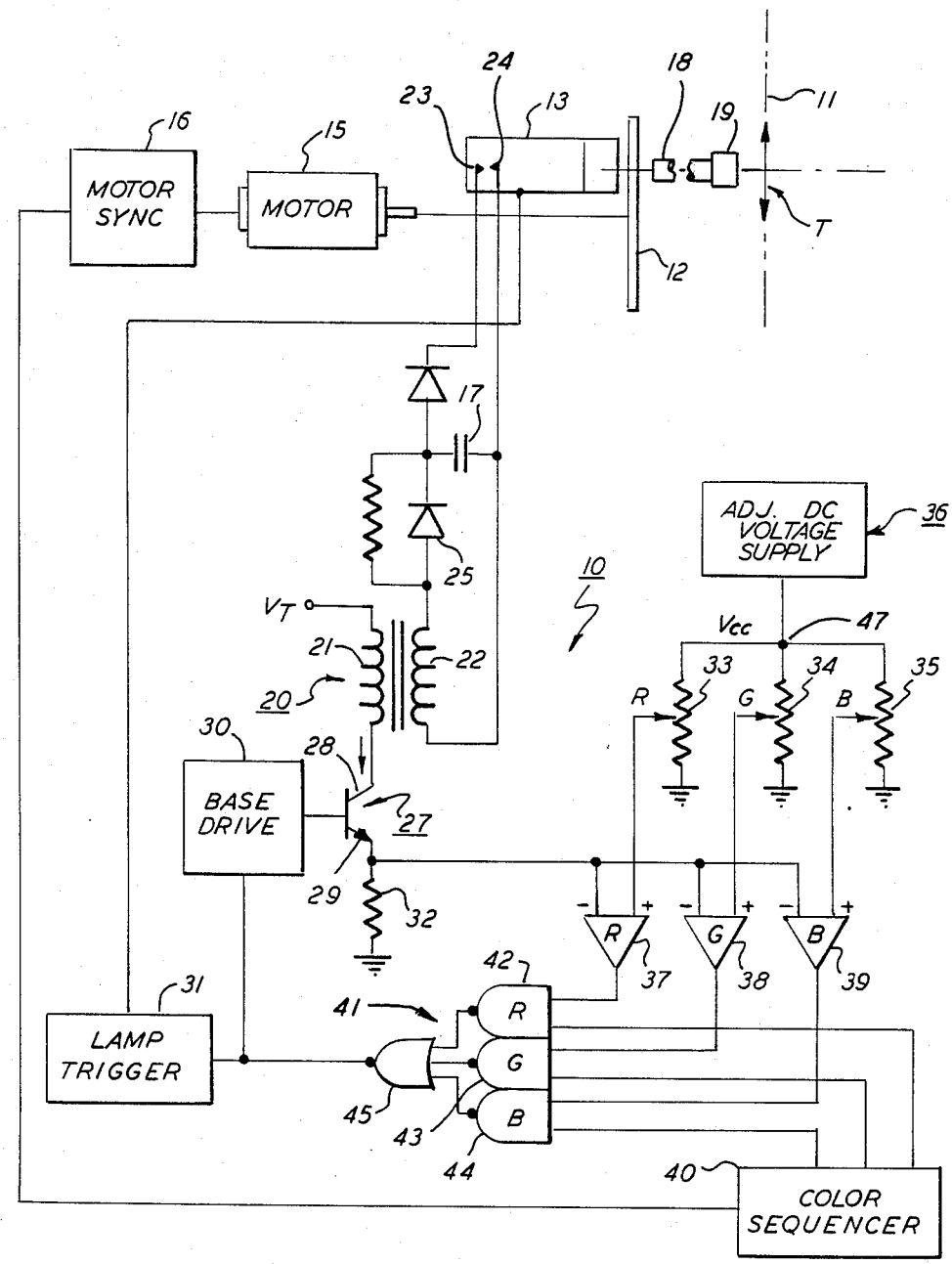
FIG. 1a illustrates a lamp system for use in illuminating the endoscope target and supporting circuitry for adjusting the intensity of the illumination output of said lamp during each video field for proportionally balancing the color-separated video images.

A video-equipped endoscope is described in reissued U.S. Pat. Nos. Re. 31,289 and Re. 31,290 to Moore et al in which a CCD-equipped camera is contained within the viewing head of the instrument. Three monochrome color images of the target are created by bringing red, green and blue light into the target region from three separate light sources via a fiber bundle. The three light sources are activated in a timed sequence with each video field to sequentially create three color-separated images of the target. The apparatus of the present invention is intended to replace the three-lamp illumination system of the Moore et al video endoscope with a single-lamp system that uses a filter wheel for achieving color separation. The disclosure contained in the Moore et al patents is herein incorporated by reference to the extent necessary for a more thorough understanding of the video system.

With reference to the drawings, there is shown an illumination system, generally referenced 10, that is intended for use in a video endoscope of the type disclosed by Moore et al in the above-noted patents. A target 11 is shown positioned in the image plane of a video camera 18 containing a single CCD image sensor and the target is arranged to be illuminated by means of a flash lamp 13 adapted to fire through a color wheel 12 to bring the illumination to the target via a fiber optics bundle 18. A series of red, green and blue filters are mounted upon the color wheel and are moved in sequence through the light path of the lamp. The color wheel is coupled directly via a shaft 14 to a synchronous motor 15 that controls the speed of the wheel through means of the motor synchronization circuit 16. Each of the three noted filters is passed sequentially through the light beam of the lamp once during every third video field. Every three fields are thus subdivided into three individual sections during which red, green and blue color information is acquired. In practice, the time duration of each color separation period is about equal and provides sufficient time for the color data to be recorded by the image sensor and clocked out of the sensor in the form of a video signal.

The light source 13 is a conventional gas-filled flash lamp which is sometimes referred to as an arc discharge lamp. As is well known in the arts, the flash lamp includes a quartz envelope that is filled with an inert gas such a xenon or the like. A high-voltage trigger pulse to the lamp from the circuit 31 is applied to the fill gas causing it to ionize and thus provide a path for current to flow between a pair of electrodes 23 and 24. Once triggered, a charge capacitor 17 contained in the lamp's discharge circuit is allowed to discharge through the electrodes to produce a high intensity flash of illumination. The intensity of the light emitted by the lamp during each flash period is directly related to the amount of voltage to which the discharge capacitor is charged and may be expressed by the relationship:

$$E = \tfrac{1}{2}CV^2 \qquad (1)$$

where:
C is the capacitance of the discharge capacitor; and
V is the stored voltage to which the capacitor is charged.

One side of the discharge capacitor 17 is connected to the secondary winding 22 of a flyback transformer 20 by means of a blocking diode 25. The primary winding 21 of the transformer, in turn, is connected in series between the collector of a Darlington transistor 27 and the transformer power supply $V_t$. A sensing resistor 32 is placed between the emitter 29 of the transistor and ground so that the voltage dropped across the resistor is directly proportional to the current flowing through the collector.

The transistor 27 is controlled by means of three separate comparators 37–39 that are connected to the base drive 30 of the transistor through a gating network generally referenced 41. As shown in the drawings, the voltage dropped over the resistor 32, which will herein be referenced to as the sensed voltage, is applied to the negative input terminal of each of the three comparators. The second or positive input terminal of each comparator, in turn, is connected to a common voltage supply $V_{cc}$ depicted at reference point 47 through means of three adjustable potentiometers 33–35. Comparator 37 and potentiometer 33 act in concert to form a red control circuit while comparator 38 and potentiometer 34 similarly form a green control circuit, and comparator 39 and potentiometer 35 form a blue control circuit. Each comparator is adapted to provide a digital zero output when the sensed voltage applied to the negative terminal equals the voltage dropped over the wiper arm of the associated potentiometer.

The output signal from each comparator is applied to one of three AND gates found in the gating network generally referenced 41. Each of the AND gates are enabled in a timed sequence by an enabling signal provided to the gate from the video sequencer 40. In practice, the red gate 42 is enabled during the red portion of the red video field, while the green gate 43 and the blue gate 44 are similarly enabled during the green and blue portions of the greeh and blue fields. The output from each AND gate is fed through a single NOR gate 45 to turn on both the lamp trigger control circuit 31 and the Darlington transistor 27 through means of its base drive circuit 30. The base drive circuit will remain on as long as a digital one is received from the gating network and correspondingly turn off the transistor when a digital zero is received.

In operation, at the beginning of a red imaging sequence, the red gate 42 is enabled by the color sequencer 40 whereby the comparator 37 is connected directly through 41 to the base drive of the transistor 27. The signal from the comparator and gating network 41 initially turns on the transistor thus providing a path for current to flow through the primary winding 21 of the flyback transformer 20. The current also flows through the sensing resistor 32 whereby the voltage dropped over the resistor is directly proportional to the amount of current flowing through the primary side of the transformer. As can be seen, shutting down the transistor terminates the current flow and the electromagnetic field on the primary side of the transformer collapses thereby inducing a voltage in the secondary winding 22. This, in turn, forward biases the blocking diode 25 and charges the lamp discharge capacitor 17 to some discernible voltage level. The voltage to which the capacitor is charged is directly related to the amount of current that is permitted to pass through the primary side of the transformer and is expressed by the following relationship:

$$\tfrac{1}{2}CV^2 = \tfrac{1}{2}(L_p \times I_p^2) \qquad (2)$$

where:

$L_p$ is the inductance of the primary winding; and
$I_p$ is the current through the primary winding.

When the voltage dropped over the sensing resistor 32 equals the value set into the red control potentiometer, the output of the red caparator goes to a digital zero thereby shutting off the transistor. This, in turn, limits the amount of charge that is stored upon the capacitor 17 during the red imaging sequence of the red video field. Once the capacitor has reached the desired charge level, the lamp is triggered through the triggering circuit so as to ionize the fill gas and thus cause the capacitor to discharge through the lamp. As noted above, the intensity of the light emitted by the lamp during the red flash period is directly related to the voltage to which the capacitor 17 is charged and is thus controlled by setting the wiper arm of the red potentiometer. The intensity of the light emitted during the green and blue illumination periods of each respective video field is similarly adjusted. Using the three potentiometer controls, the three primary colors presented in the video picture can be finely balanced to a point where the colors displayed on the video screen accurately reflect the colors found in the target.

Figure 1B:
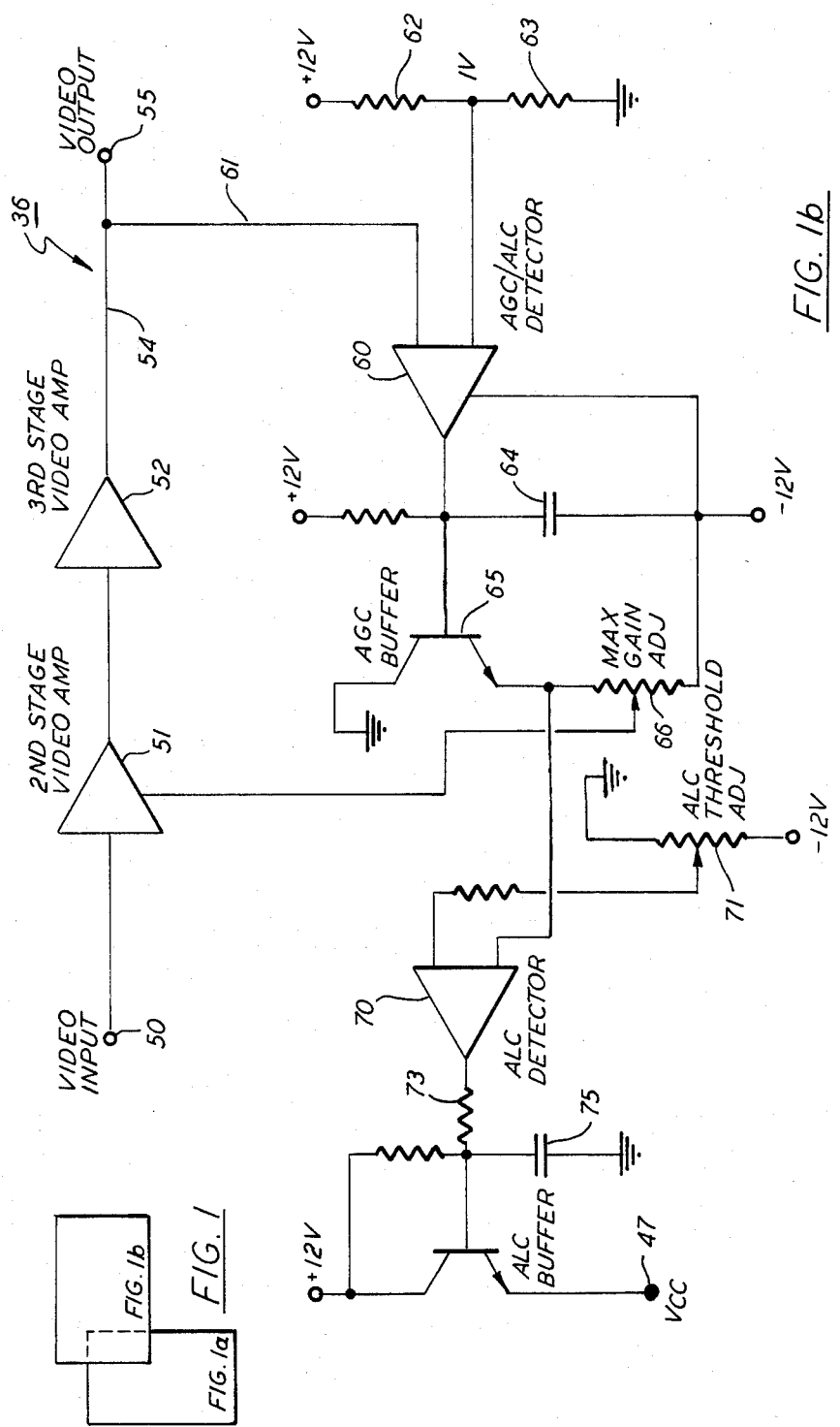
FIG. 1b illustrates further circuit means for controlling the gain of the video amplifier section and the intensity of the illumination lamp in response to the video signal level that is applied to the video processor.

Referring now to FIG. 1b, there is shown further circuitry for automatically controlling the video signal level sent to the video processor of the endoscope. As is well known in the art, the viewing head 19 of the instrument is constantly being adjusted and repositioned within a relatively confined enclosure or body cavity as the insertion tube is steered by the operator. The intensity of the reflected target image falling on the CCD image sensor can increase to such a high level that the sensor will reach saturation or a full well condition thereby causing the video picture to bloom. By the same token, as the insertion head moves away from the target region, the image intensity can fall off dramatically to a very low level again degrading the picture information. As will be explained in further detail below, the apparatus of the present invention is capable of automatically controlling the video signal levels to compensate for such changes in the image intensity.

The CCD image sensor integrates the light imaged onto its recording surface when processing a given target picture. As previously noted, the illumination strobe lamp can be flashed many times during each illumination sequence or interval to obtain peak total brightness without having to alter the balance between the strobes producing different colors of illumination. A technique will be herein described for coupling an illumination control with an automatic gain control to achieve high quality video images over a wide variation in target scenes while simultaneously operating the image sensor at near optimum signal levels that are well above background noise and which approach but do not attain saturation of the CCD.

FIG. 1b is a circuit diagram outlining this technique. The video signals coming from the image sensor are applied to input terminal 50 and from there carried to a series of amplifiers via line 54. The signals are passed through two stages of video amplification 51 and 52 before being passed on to the video processor at terminal 55. The second stage video amplifier 51 is a variable gain amplifier. The output of the video amplifiers is monitored by an AGC/ALC detector 60 via input line 61.

The AGC/ALC detector is arranged to compare the video signal level with a second signal provided by the resistor network made up of resistors 62 and 63. The detector is set so that when the level of the video signal approaches the level at which the video picture blooms, the detector will turn on thereby providing an output signal. When the detector turns on, capacitor 64 in the output circuit thereof is allowed to discharge back through the detector network. As the voltage on the capacitor decreases, the voltage on the emitter side of the AGC buffer transistor 65 correspondingly decreases. The buffer transistor 65 is a continually operating voltage follower. An adjustable resistor 66 is placed between the buffer emitter and a negative 12-volt supply. A feedback signal is developed over the adjustable resistor which is used to control the gain of the variable gain amplifier 51. The resistor 66 is adjusted so that the gain of the amplifier is reduced when the level of the video signal approaches an amplitude at which the video picture displayed on the video tube begins to bloom. As can be seen, the AGC/ALC detector and the AGC buffer combine to establish a conventional automatic gain control route that can be adjusted to provide a given peak-to-peak output from a wide range of input signals. Besides certain circuit limitations, there are other considerations that might constrain the usable and desirable range of the automatically-controlled gain circuit. For example, if the signals from the image sensor are large to a point of saturation, the automatic gain control output will be extremely low. Similarly if the image sensor video output is relatively low, the AGC gain will have to be correspondingly high and therefore enhance noise in the image regions.

In the present technique, the automatic gain control loop is coupled to an automatic lamp control circuit to eliminate the above-noted problems. These two control circuits operate on precisely the same decision-making principles and thus can be easily coupled.

A second automatic light control (ALC) detector 70 is connected to the emitter of the automatic gain control buffer 65 so as to sense the emitter voltage. The second detector is adapted to turn on when the threshold voltage set into the ALC adjustable threshold resistor 71 is exceeded. Upon turning on, the output of the ALC detector will go to a minus 12 volts and current will flow through resistor 73 in the output circuit causing capacitor 75 to discharge. As the voltage on the capacitor drops below a positive 12 volts, the voltage at the emitter of the ALC buffer transistor 77 correspondingly decreases. The ALC buffer, like the AGC buffer, is a continually-operating voltage follower and is arranged in the light control circuit to determine the level of supply voltage $V_{cc}$ provided to the three light amplitude potentiometers 33–35. As previously noted, the lamp driver circuitry 10 is designed so that the individual color light amplitudes are directly proportional to the voltage on the potentiometer wiper arms. The wiper arm voltage, in turn, is directly proportional to the ALC supply voltage $V_{cc}$. As a result of this relationship, a given percentage change in the supply voltage at point 47 will result in a like percentage change in each of the three individual light outputs. Accordingly, the selected color balance which has been set into the controls 33–35 will be maintained while the light output is being automatically controlled by means of the ALC circuitry. By using this technique, continuous light reduction to a near zero light level can be obtained without disturbing the color balance of the system.

In practice, the first AGC/ALC detector 60 is preset to turn on when the video signal reaches a pre-selected level whereby optimum video pictures are attained. The second ALC detector 70, which is coupled in series to the output of the first detector, is adapted through the adjustable ALC threshold resistor 71 to turn on at a point just before that at which the CCD begins to saturate or bloom, that is, at a point where the gain control of the video amplifier cannot be reduced any further without also reducing the light intensity to prevent the CCD from blooming. When the ALC detector is turned on, the common supply voltage provided to each of the individual lamp amplitude control circuits is reduced thereby reducing the illumination output of the lamp without affecting the color balance of the system.

While this invention has been described with reference to the structure disclosed herein, it is not confined to the details as set forth and this application is intended to cover any modifications or changes as may come within the scope of the following claims.

I claim:

1. In a video endoscope having a solid state image sensor located in the viewing head of an instrument for recording light images of a target and clocking out the image data in the form of a video signal, a video signal level control apparatus that includes a lamp for illuminating a target in the viewing range of the image sensor whereby image data of the target recorded by the sensor is clocked out as a video signal, a color wheel for passing a series of different color filters in series through the illumination beam of the lamp in synchronism with each video field to image the target sequentially with light of each different color in synchronism with each said field, lamp driver means having an individual lamp amplitude control for regulating the illumination intensity of the lamp during each color imaging sequence, each lamp amplitude control having an adjustable voltage divider for connecting the lamp to a common voltage supply so that the color intensity of the images recorded by the sensor during a field can be proportionally balanced, detector means for sensing the level of the video signals clocked out of the image sensor and providing a variable output signal indicative of the video signal level, and adjusting means for automatically regulating the common supply voltage to the lamp amplitude controls in response to the said variable output signal of the detector means to maintain the video signal at a desired level without disturbing the balance of the recorded color images.

2. The apparatus of claim 1 that further includes a variable gain video amplifier for adjusting the gain of the said video signal and wherein the detector means includes a first comparator means for sensing the video output level of the amplifier and automatically adjusting the amplifier gain when the level of the video signal exceeds a first predetermined level.

3. The apparatus of claim 2 wherein the detector means further includes a second comparator means for sensing the output of the first comparator and automatically adjusting the common voltage supplied to the said lamp amplitude controls when the output of the first comparator reaches a second predetermined level.

4. The apparatus of claim 3 wherein said second comparator means further includes means for adjusting said predetermined level to a point just below the level at which the solid state imager reaches saturation.

5. The apparatus of claim 1 wherein the color wheel contains a red, a green and a blue filter to create three color-imaging sequences in sychronism with each field and the lamp drive contains a red amplitude control, a green amplitude control and a blue amplitude control.

6. The method of controlling the signal level of a video endoscope having a single lamp for illuminating a target and a color wheel for passing different color filters through the illumination beam of the lamp in sychronism with each video field to provide color-separated images of the target, providing a solid state image sensor for sequentially recording the color-separated images in sychronism with each field and clocking out the image data as a video signal, setting the illumination intensity of the lamp during each color imaging sequence so that the color images are proportionally balanced, sensing the level of the video signal clocked out of the image sensor, and equally adjusting the illumination intensity of the lamp during each color imaging sequence to maintain the video signal at a desired level without disturbing the color balance.

7. The method of claim 6 that further includes the step of controlling the output gain of the video signal to a first signal level and subsequently adjusting the illumination intensity of the lamp when the input signal level rises to a level above that which produces the first output level.

* * * * *